(12) United States Patent
Björk et al.

(10) Patent No.: US 6,605,616 B1
(45) Date of Patent: *Aug. 12, 2003

(54) QUINOLINE DERIVATIVES

(75) Inventors: Anders Björk, Bjärred (SE); Stig Jönsson, Lund (SE); Tomas Fex, Lund (SE); Gunnar Hedlund, Lund (SE)

(73) Assignee: Active Biotech AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/621,486

(22) Filed: Jul. 21, 2000

Related U.S. Application Data

(63) Continuation of application No. 09/352,886, filed on Jul. 14, 1999, now Pat. No. 6,133,285.
(60) Provisional application No. 60/092,967, filed on Jul. 15, 1998.

(51) Int. Cl.⁷ .................. A61K 31/4704; C07D 215/56; A61P 29/00; A61P 37/00

(52) U.S. Cl. ..................... 514/312; 514/232.8; 514/291; 546/90; 546/155; 544/128

(58) Field of Search .................. 546/90, 155; 544/128; 514/232.8, 291, 312

(56) References Cited

U.S. PATENT DOCUMENTS

| | | | |
|---|---|---|---|
| 4,547,511 A | * 10/1985 | Eriksoo et al. | 514/312 |
| 4,738,971 A | * 4/1988 | Eriksoo et al. | 514/312 |
| 5,580,882 A | * 12/1996 | Abramsky et al. | 514/312 |
| 5,594,005 A | * 1/1997 | Slavin et al. | 514/311 |
| 5,726,183 A | 3/1998 | Nilsson | |
| 5,728,713 A | 3/1998 | Nilsson | |

FOREIGN PATENT DOCUMENTS

| | | |
|---|---|---|
| EP | 0 059 698 | 9/1982 |
| GB | 2 290 786 | 1/1996 |
| WO | 92-18483 | 10/1992 |
| WO | 95-24195 | 9/1995 |
| WO | 95-24196 | 9/1995 |
| WO | 95-24395 | 9/1995 |

OTHER PUBLICATIONS

Andersen et al, "Linomide reduced the rate of active lesions in relapsing–remitting multiple sclerosis", *Neurology* 47:895–900 (1996).

Bai et al, "Linomide–induced suppression of experimental autoimmune neuritis is associated with down–regulated macrophage function", *J. Neuroimmunol.* 76:177–184 (1997).

Gonzalo et al, "Linomide, a novel immunomodulator that prevents death in four models of septic shock", *Eur. J. Immunol.* 23:2372–2374 (1993).

Gonzalo et al, "Linomide inhibits programmed cell death of peripheral T cells in vivo", *Eur. J. Immunol.* 24:48–52 (1994).

Gross et al, "Prevention of diabetes mellitus in non–obese diabetic mice by linomide, a novel immunomodulating drug", *Diabetologia* 37:1195–1201 (1994).

Harcourt, "Polyarteritis in colony of beagles", *The Veterinary Records,* 102:519–522 (1978).

Kalland, "Regulation of Natural Killer Progenitors", *J. Immunol.* 144:4472–4476 (1990).

Karussis et al, "Treatment of chronic–relapsing experimental autoimmune encephalomyelitis with the synthetic immunomodulator linomide (quinoline–3–carboxamide)", *Proc. Natl. Acad. Sci.* 90:6400–6404 (1993).

Karussis et al, "Immunomodulation of experimental autoimmune myasthenia gravis with linomide", *J. Neuroimmunol.* 55:187–193 (1994).

Karussis et al, Treatment of secondary progressive multiple sclerosis with the immunomodulator linomide, *Neurology* 47:341–346 (1996).

Larrson, "Mechanism of Action in the New Immunomodulator LS2616 on T cells Response", *Int. J. Immunol.* 9(4):426–431 (1987).

(List continued on next page.)

*Primary Examiner*—Evelyn Mei Huang
(74) *Attorney, Agent, or Firm*—Browdy and Neimark, P.L.L.C.

(57) ABSTRACT

The invention is related to compounds of general formula (I)

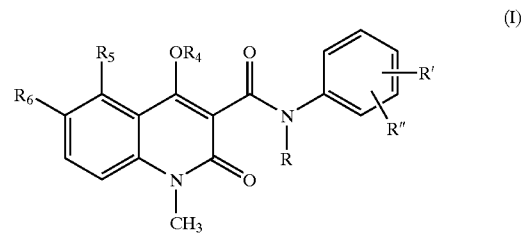

wherein R is methyl, ethyl, n-propyl, iso-propyl, n-butyl or allyl; R' is methyl, methoxy, fluoro, chloro, bromo, azido, trifluorometlhyl, or $OCH_xF_y$, wherein x=0–2, y=1–3 with the. proviso that x+y=3; R" is hydrogen, fluoro or chloro; with the proviso that R" is fluoro or chloro only when R' is fluoro or chloro; $R_4$ is hydrogen or pharmaceutically acceptable inorganic or organic cations; $R_5$ is dimethylamino or nitro; $R_6$ is hydrogen; and when R' is azido $R_5$ is also ethyl, n-propyl, iso-propyl, methoxy, ethoxy, chloro, bromo, trifluoromethyl, $OCH_xF_y$, wherein x=0–2, y=1–3 with the proviso that x+y=3, or $R_5$ and $R_6$ taken together are methylenedioxy; and any tautomer thereof. The invention also relates to pharmaceutical compositions containing a compound of the general formula (I) together with a pharmaceutically acceptable carrier. Included are also processes for the preparation of the compounds of formula (I), as well as methods for the treatment of mammals suffering from diseases resulting from autoimmunity and pathological inflammation by administering of a compound having the formula (I) to said mammal.

18 Claims, No Drawings

OTHER PUBLICATIONS

Prineas, "The neuropathology of multiple sclerosis", *Handbook of Clinical Neurology* 3(47):213–257 (1985).

Tarkowski et al, "Successful Treatment of Autoimmunity in MRL/1 Mice with LS–2616, a new immunomodulator", *Arthritis and Rheumatism* 29(11):1405–1409 (1986).

Wanders et al, "Abolition of the Effects of Cyclosporine on Rat Cardiac Allograft Rejection by the New Immunomodulator LS–2616 (Linomide)", *Transplantation* 47:216–217 (1989).

Abstract: Japanese patent No. 07224040; Aug. 8, 1995.

Abstract: Japanese patent No. 07252228; Oct. 3, 1995.

* cited by examiner

QUINOLINE DERIVATIVES

CROSS REFERENCE TO RELATED APPLICATION

This is a continuation in part of U.S. application Ser. No. 09/352,886, filed Jul. 14, 1999, U.S. Pat. No. 6,133,285, which claims the benefit of U.S. provisional application No. 60/092,967, filed Jul. 15, 1998, now abandoned.

FIELD OF THE INVENTION

The present invention relates to novel substituted quinoline-3-carboxamide derivatives, to methods for their preparation, to compositions containing them, and to methods and use for clinical treatment of diseases resulting from autoimmunity, such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease. More particularly, the present invention relates to novel quinoline derivatives suitable for the treatment of, for example, multiple sclerosis and its manifestations.

BACKGROUND OF THE INVENTION

Autoimmune diseases, e.g., multiple sclerosis (MS), insulin-dependent diabetes mellitus (IDDM), systemic lupuis erythematosus (SLE), rheumatoid arthritis (RA), inflammatory bowel disease (IBD) and psoriasis represent assaults by the body's immune system which may be systemic in nature, or else directed at individual organs in the body. They appear to be diseases in which the immune system makes mistakes and, instead of mediating protective functions, becomes the aggressor (1).

MS is the most common acquired neurologic disease of young adults in western Europe and North America. It accounts for more disability and financial loss, both in lost income and in medical care, than any other neurologic disease of this age group. There are approximately 250.000 cases of MS in the United States. Although the cause of MS is unknown, advances in brain imaging, immunology, and molecular biology have increased researchers' understanding of this disease. Several therapies are currently being used to treat MS, but no single treatment has demonstrated dramatic treatment efficacy. Current treatment of MS falls into three categories: treatment of acute exacerbations, modulation of progressive disease, and therapy for specific symptoms.

MS affects the central nervous system and involves a demyelination process, i.e., the myelin sheaths are lost whereas the axons are preserved. Myelin provides the isolating material that enables rapid nerve impulse conduction. Evidently, in demyelination, this property is lost. Although the pathogenic mechanisms responsible for MS are not understood, several lines of evidence indicate that demyelination has an immunopathologic basis. The pathologic lesions, the plaques, are characterized by infiltration of immunologically active cells such as macrophages and activated T cells (2).

In U.S. Pat. No. 4,547,511 and in U.S. Pat. No. 4,738,971 and in EP 59,698 some derivatives of N-aryl-1,2-dihydro-4-substituted-1-alkyl-2-oxo-quinoline-3-carboxamide are claimed as enhancers of cell-mediated immunity. The compound

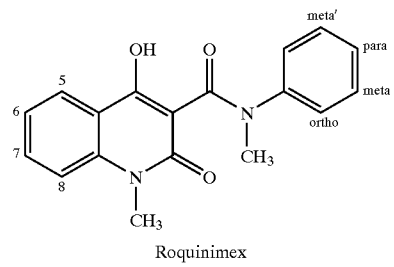

Roquinimex known as roquinimex (Merck Index 12th Ed., No. 8418; Linomide®, LS2616, N-phenyl-N-methyl-1,2-dihydro-4-hydroxy-1-methyl-2-oxo-quinoline-3-carboxamide) belongs to this series of compounds. Roquinimex has been reported to have multiple immunomodulatory activities not accompanied with general immunosuppression (3–12). Furthermore, in U.S. Pat. No. 5,580,882 quinoline-3-carboxarnide derivatives are claimed to be useful in the treatment of conditions associated with MS. The particular preferred compound is roquinimex. In U.S. Pat. No. 5,594,005 quinoline-3-carboxamide derivatives are claimed to be useful in the treatment of type I diabetes. The particular preferred compound is roquinimex. In WO 95/24195 quinoline-3-carboxamide derivatives are claimed to be useful in the treatment of inflammatory bowel disease. Particularly preferred compounds are roquinimex or a salt thereof. In WO95/24196 quinoline-3-carboxamide derivatives are claimed to be useful in the treatment of psoriasis. Particularly preferred compounds are roquinimex or a salt thereof.

In clinical trials comparing roquinimex to placebo, roquinimex was reported to hold promise in the treatment of conditions associated with MS (13, 14). There are, however, some serious drawbacks connected to roquinimex. For example, it has been found to be teratogenic in the rat, and to induce dose-limiting side effects in man, e.g., a flu-like syndrome, which prevents from using the full clinical potential of the compound.

Further, in WO 92/18483 quinoline derivatives substituted in the 6-position with a $R_AS(O)_n$-group ($R_A$=lower alkyl or aryl; n=0–2) are claimed, which possess an immunomodulating, anti-inflammatory and anti-cancer effect.

The substitution, i.e., type and pattern, of the above, specifically mentioned, compounds in the prior art places them outside the scope of the present invention.

DESCRIPTION OF THE INVENTION

A primary objective of the present invention is to provide structurally novel quinoline compounds which by virtue of their pharmacological profile, with high potency in experimental models and low level of side-effects, are considered to be of value in the treatment of disease resulting from autoimmunity and pathologic inflammation. Examples of such diseases are multiple sclerosis, insulin-dependent diabetes mellitus, systemic lupus erythematosus, rheumatoid arthritis, inflammatory bowel disease and psoriasis and other diseases where inflammation plays a major role, such as asthma, atherosclerosis, stroke and Alzheimer's disease. More particularly, the present invention relates to novel quinoline derivatives suitable for the treatment of, for example, multiple sclerosis and its manifestations.

The term "treatment" as used herein includes prophylaxis as well as relieving the symptoms of disease.

It has now surprisingly been found that the novel compounds of general formula (I)

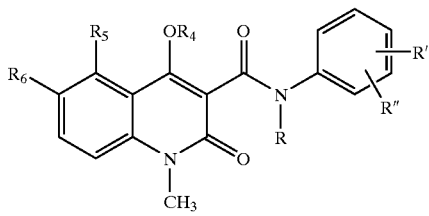

wherein
- R is selected from methyl, ethyl, n-propyl, iso-propyl, n-butyl and allyl;
- R' is selected from methyl, methoxy, fluoro, chloro, bromo, azido, trifluoromethyl, and $OCH_xF_y$, wherein $x=0-2$, $y=1-3$ with the proviso that $x+y=3$;
- R" is selected from hydrogen, fluoro and chloro, with the proviso that R" is selected from fluoro and chloro only when R' is selected from fluoro and chloro;
- $R_4$ is selected from hydrogen and pharmaceutically acceptable inorganic cations, such as sodium, potassium and calcium, and organic cations such as monoethanolamine, diethanolamine, dimethylaminoethanol, morpholine and the like;
- $R_5$ is selected from dimethylamino, and nitro;
- $R_6$ is hydrogen,
- and when R' is azido then $R_5$ is selected from ethyl, n-propyl, methoxy, ethoxy, chloro, bromo, trifluoromethyl, and $OCH_xF_y$, wherein $x=0-2$, $y=1-3$ with the proviso that $x+y=3$;
- or $R_5$ and $R_6$ taken together are methylenedioxy;

are unexpectedly effective and specific in the treatment of individuals suffering from autoimmune and inflammatory diseases.

The compounds of general formula (I) may exist in different tautomeric forms and all such forms where such forms exist are included herein.

In a preferred embodiment of the invention $R_4$ is selected from hydrogen or sodium,
- $R_5$ is dimethylamino,
- R is selected from methyl and ethyl,
- R' is selected from methyl, methoxy, fluoro, chloro and parca-azido when R" is hydrogen and
- R" is selected from meta'- and para-fluoro provided that R' is ortho-fluoro.

Among the most preferred compounds of general formula (I) according to the present invention are:

N-methyl-N-(4-azido-phenyl)-1,2-dihydro-4-hydroxy-5-chloro-1-methyl-2-oxo-quinoline-3-carboxamide, N-ethyl-N-(4-azido-phenyl)-1,2-dihydro-4-hydroxy-5-chloro-1-methyl-2-oxo-quinoline-3-carboxamide, N-methyl-N-(4-azido-phenyl)-1,2-dihydro-4-hydroxy-5,6-methylenedioxy-1-methyl-2-oxo-quinoline-3-carboxamide, N-ethyl-N-(4-azido-phenyl)-1,2-dihydro-4-hydroxy-5,6-methylenedioxy-1-methyl-2-oxo-quinoline-3-carboxamide, N-methyl-N-(4-methoxy-phenyl)-1,2-dihydro-4-hydroxy-5-dimethylamino-1-methyl-2-oxo-quinoline-3-carboxamide, N-methyl-N-(2,5-difluoro-phenyl)-1,2-dihydro-4-hydroxy-5-dimethylamino-1-methyl-2-oxo-quinoline-3-carboxamide.

Several spontaneously occurring autoimmune diseases in man have experimental models that are spontaneously occurring in certain strains of laboratory animals or can be induced in laboratory animals by immunization with specific antigen(s) from the target organ.

Experimental autoimmune encephalonmyelitis (EAE) as a model for autoimmune inflammatory diseases of the central nervous system (CNS) has been the most widely used model for the human disease multiple sclerosis. Autoimmunity to type II collagen can experimentally be induced in certain strains of mice or rats and may lead to the development of polyarthritis. The collagen-induced arthritis has several features in common with the human disorder rheumatoid arthritis.

The hallmark of asthma in humans is an increased reactivity of the airways to a range of chemical and physical stimuli. It is now widely accepted that products released from inflammatory cells, e.g., activated eosinophils, compromise epithelial integrity and promote bronchial hyperresponsiveness. The murine model of ovalbumin (OA)-induced lung inflammation is dominated by the temporally regulated influx of lymphocytes and eosinophils into the bronchial lumen.

Roquinimex has been found to induce the Beagle Pain Syndrome (BPS) (15, 16) in different breeds of beagle dogs. The disease is reflected by clinical and laboratory manifestations justifying BPS as a model for the flu-like syndrome induced by roquinimex in man.

The compounds of general formula (I) were assayed for inhibition of acute experimental autoimmune encephalomyelitis (aEAE) in mice. Roquinimex was used as treatment control and showed a more than 50% inhibition at $\geq 5$ mg/kg. Surprising and unexpected results were obtained when introducing proper substitution in the 5-position of the quinoline ring. In comparison with roquinimex, the potency of the 5-chloro substituted compound was increased a 100-fold. Substitution in the 6-, 7-, and 8-position resulted in less active compounds. The effect of the 5-substitution could largely be understood on physicochemical grounds. In general, the EAE activity as seen by the EAE inhibition was in the following descending order according to the position of the substitution: 5>6>>7=8. Furthermore, proper aromatic substitution in the quinoline moiety and the 3-carboxamide moiety of the compounds of general formula (I) significantly reduced or even abolished the side effects, i.e., the teratogenic effect and the BPS, of roquinimex. Thus, physicochemical properties of the 5-substituent in the quinoline moiety and the ortho-, meta- and/or, in particular, the para-substituent in the 3-carboxamide moiety are of major importance for an improved risk/benefit ratio in comparison with roquinimex. Replacement of the methyl group on the carboxamide nitrogen with a higher alkyl group reduced the side effects even further. Hence, the compounds of formula (I) have surprisingly been found to be both chemically and pharmacologically different from those drugs hitherto suggested for the treatment of MS and its manifestations.

All embodiments of the invention as disclosed in the claims are herewith included in the specification.

The following examples are intended to illustrate the invention without restricting the scope thereof The compounds of general formula (I) may be prepared by methods known in the literature and the following methods:

Method A:

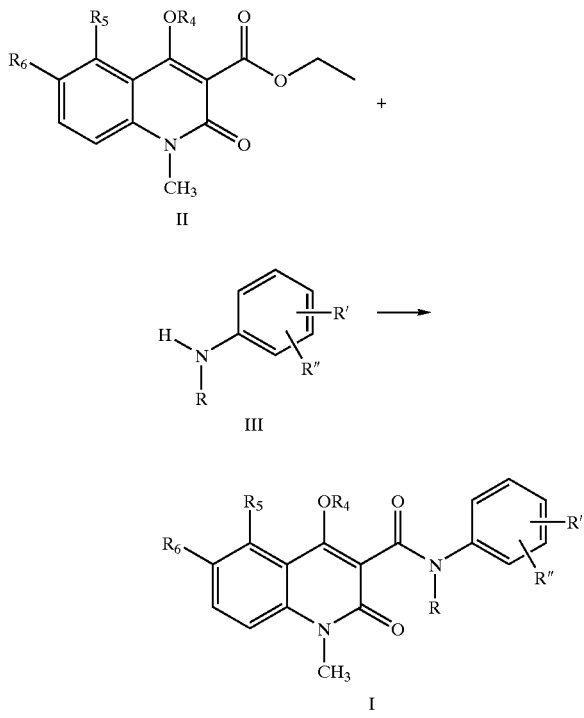

The compounds of general formula (I) may be prepared by known methods and, for example, as shown above, by reaction of an ester derivative of the quinoline carboxylic acid with an aniline in a suitable solvent such as toluene, xylene and the like. General methods for preparation of the quinoline carboxylic acid ester derivatives of formula (II) are described below. N-alkylated anilines of formula (III) are commercially available or known from literature, e.g., in Johnstone et al., J. Chem. Soc. 1969, 2223–2224. Compounds falling within the scope of formula (III) may be prepared by methods, which are generally analogous to those of said literature.

Method B:

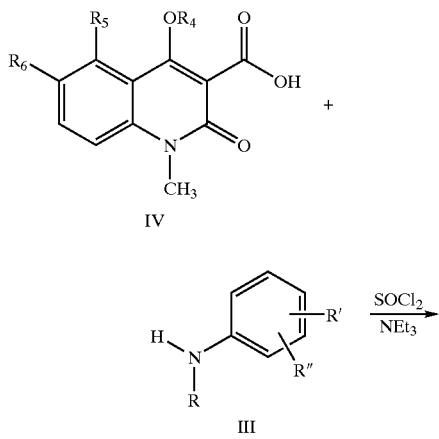

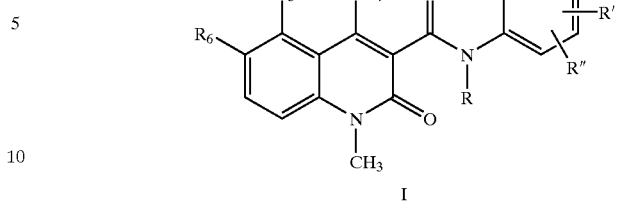

The compounds of formula (I) may also be prepared by reaction of a quinoline carboxylic acid of formula (IV) with an aniline of formula (III). Various coupling reagents known in the art may be used, e.g., carbodiimides known from literature in U.S. Pat. No. 4,547,511. One suitable coupling method utilizes thionyl chloride in the presence of triethylamine and a suitable solvent such as dichloromethane. This method may be used in instances when direct coupling between ester and aniline does not work, e.g., when the aniline contains electron-withdrawing substituents. The quinoline carboxylic acids of formula (IV) may be obtained from the corresponding esters of formula (II) by acidic hydrolysis as described below.

EXAMPLE 1

1,2-Dihydro-4-hydroxy-5-dimethylamino-1-methyl-2-oxo-quinoline-3-carboxylic Acid Ethyl Ester A solution of 2,6-difluorobenzonitrile (35.7 g, 0.26 mol) and dimethylamine (17.5 g, 0.39 mol) in 100 ml of anhydrous isopropanol was heated at 110° C. for 18 hours in an autoclave. After cooling, the solvents were evaporated and the residue worked up with water and diethyl ether to give a yellowish oil (41 g) of 2-dimethylamino-6-fluorobenzonitrile contaminated with 2–4% of 2,6-di (dimethylamino)benzonitrile. This crude mixture was solved in 40% aqueous methylamine (130 ml, 1.5 mol) and ethanol (100 ml) and heated at 110° C. for 18 hours in an autoclave. The product was worked up as above to give 44 g of 2-dimethylamino-6-methylaminobenzonitrile (>95% pure). The benzonitrile was hydrolyzed in conc. sulfuric acid (170 ml) and water (34 ml) at 120° C. for 3 hours. The brown solution was cooled and neutralized with 5 M sodium hydroxide. The resulting cloudy mixture was filtered through celite and washed with 30 ml of diethyl ether. Then the aqueous solution was extracted with dichloromethane (3×50 ml), the extracts were washed with water and evaporated to give a pure grey-reddish 6-dimethylamino-N-methyl-anthranilic acid. The anthranilic acid (21.5 g, 0.11 mol) was dissolved in 250 ml of 1,4-dioxane. Phosgene (25 ml, 0.45 mol) was slowly added under cooling in an ice bath. The mixture was warmed at 40° C. for 1 hour, cooled to 15° C., and then the product was collected by filtration. This was worked up with aqueous sodium bicarbonate and dichloromethane. The organ phase was carefully dried and evaporated to give the pure 5-dimethylamino-N-methyl-isatoic anhydride. The isatoic anhydride (22 g, 0.10 mol) was dissolved in anhydrous methanol (150 ml) and sodium methoxide (5.4 g, 0.10 mol) was added. After stirring at 50° C. for 3 hours, the solvent was removed and the residue worked up with water and ether to give 6-dimethylamino-N-methyl-anthranilic acid methyl ester as a yellow oil (15 g). The oil (10.4 g, 0.05 mol), was dissolved in dichloromethane (100 ml) and cooled on an ice-bath and ethyl malonyl chloride (10 g, 0.07 mol) was added. After being stirred for 1 hour at room temperature, the cloudy mixture was washed with aqueous sodium bicarbonate. The organic phase was carefully dried and concentrated under vacuum. The residue was then dissolved in dry ethanol (100 ml) and sodium methoxide (9 g, 0.16 mol) was added. The mixture was stirred for 1 hour, neutralized with hydrochloric acid, the solvent was removed and the residue worked up with water and dichloromethane. The organic phase was dried and the solvent removed to give the title compound as pure greyish crystals (11 g).

1H NMR (CDCl$_3$) δ 1.36 (3H, t), 2.78 (6H, s), 3.59 (3H, s), 4.39 (2H, q), 7.17 (1H, d), 7.21 (1H, d), 7.54 (1H, t), 17.1 (1H, s).

EXAMPLE 2

1,2-Dihydro-4-hydroxy-5-nitro-1-methyl-2-oxo-quinoline-3-carboxylic Acid Ethyl Ester A mixture of 2-methyl-3-nitroaniline (54.8 g, 0.36 mol) and ethyl chloroformate (100 ml, 1 mol) in 1,4-dioxane (500 ml) was heated at 65° C. for 24 hours. The clear solution was evaporated to dryness to give white crystals in quantitative yield. The crystals were dissolved in pyridine (250 ml) and water (250 ml) and warmed to 80° C. Potassium permanganate (142 g, 0.9 mol) was added portionwise during 4 hours, maintaining the temperature at 80–95° C. After another 1 hour, the black mixture was filtered through celite and the manganese dioxide cake was carefully washed with hot water (800 ml). The collected yellowish mother-liquor was treated with conc. hydrochloric acid to adjust the pH to 3–4 and then extracted with dichloromethane. The organic solvent was removed and the residue was worked up with aq. sodium bicarbonate (100 ml), unsolved material was filtered off, and the solution was acidified to give pure orange colored crystals. This benzoic acid (10 g, 0.04 mol) was dissolved in 1,4-dioxane (40 ml) and thionyl chloride (7.2 g. 0.06 mol) was added. The mixture was warmed at 50° C. during night, cooled, and the formed 5-nitro-isatoic anhydride was collected by filtration and dried. The anhydride (6.4 g, 0.031 mol) was dissolved in N,N-dimethylacetanide (30 ml) and sodium hydride (75%) (2.6 g, 0.08 mol) was added portionwise. Then, methyl iodide (5.3 g, 0.037 mol) was added and the mixture stirred for 30 minutes. Diethyl malonate (8.9 g, 0.056 mol) was added and the mixture warmed to 100° C. and stirred at this temperature for 6 hours. After cooling, water (120 ml) was added and the pH adjusted to 3–4. On standing a crystalline precipitate was formed which was filtered off, washed with water, and dried to give the title compound as beige crystals (7.1 g).

1H NMR (CDCl$_3$) δ 1.49 (3H, t), 3.73 (3H, s), 4.53 (2H, q), 7.21 (1H, d), 7.47 (1H, d), 7.72 (1H, t), 14.7 (1H, s).

EXAMPLE 3

1,2-Dihydro-4-hydroxy-5-methoxy-1-methyl-2-oxo-quinoline-3-carboxylic Acid

While cooling, 10 ml of conc. hydrochloric acid was added to 30 ml of acetic anhydride. To this solution 1,2-dihydro-4-hydroxy-5-methoxy-1-methyl-2-oxo-quinoline-3-carboxylic acid ethyl ester (10.5 g, 38 mmol) was added and the mixture heated at 80° C. for 14 hours. The mixture was cooled to room temperature and the crystalline product was filtered off, washed with cold methanol and dried to give the title compound (7.2 g), yield 77%.

1H NMR ((CDCl$_3$) δ 3.73 (3H, s) 4.02 (3H, s), 6.82 (1H, d), 7.02 (1H, d), 7.62 (1H, t).

EXAMPLE 4

N-Methyl-N-phenyl-1,2-dihydro-4-hydroxy-5-methoxy-1-methyl-2-oxo-quinoline-3-carboxamide (not Included in the Claims) (Method A)

N-Methylaniline (2.7g, 0.025 mol) was dissolved in 80 ml of toluene and about 30 ml of the solvent was distilled off in order to obtain a dry solution. 1,2-Dihydro-4-hydroxy-5-methoxy-1-methyl-2-oxo-quinoline-3-carboxylic acid ethyl ester (2.7 g, 0.01 mol) was added to the boiling solution. The ethanol formed during the reaction was distilled off together with some toluene for about 4 hours. The mixture was cooled to room temperature. The precipitate was collected, washed with cold toluene and hexane and dried to give the title compound (2.8 g), yield 83%.

1H NMR (CDCl$_3$) δ 3.49 (3H, s), 3.50 (3H, s), 4.03 (3H, s), 6.66 (1H, d), 6.86 (1H, d), 7.08–7.48 (6H, m). 13C NMR (CDCl$_3$) δ 29.7 (CH3), 36.8 (CH3), 56.8 (CH3), 103.3 (CH), 104.2 (C), 108.4 (CH), 110.2 (C), 126.2 (CH), 127.2 (CH), 128.6 (CH), 131.4 (CH), 141.2 (C), 143.6 (C), 157.0 (C), 157.4 (C), 160.3 (C), 165.1 (C). ESI MS/MS [M+H]$^+$ 339, fragment 232.

In essentially the same manner the following compounds were obtained from the corresponding starting materials:

N-methyl-N-(4-methoxy-phenyl)-1,2-dihydro-4-hydroxy-5-dimethylamino-1-methyl-2-oxo-quinoline-3-carboxamide, 1H NMR (CDCl$_3$) δ (major form) 2.66 (3H, s), 2.78 (3H, s), 3.43 (3H, s), 3.52 (3H, s), 3.69 (3H, s), 6.68 (2H, d), 7.11 (2H, t), 7.34 (2H, d), 7.47 (1H, t), 16.0 (1H, s, broad). 13C NMR (CDCl$_3$) δ 29.5 (CH3), 37.0 (CH3), 45.3 (CH3), 46.4 (CH3), 55.3 (CH3), 109.7 (C), 110.3 (C), 113.0 (CH), 113.6+113.6 (CH), 114.1 (CH), 127.6+127.6 (CH), 130.8 (C), 137.1 (C), 140.8 (C), 150.6 (C), 158.4 (C), 159.8 (C), 160.6 (C=O), 165.9 (C=O). ESI MS/MS [M+H]$^+$ 382, fragment 245.

N-methyl-N-(4-methyl-phenyl)-1,2-dihydro-4-hydroxy-5-dimethylamino-1-methyl-2-oxo-quinoline-3-carboxamide, N-methyl-N-(2,5-difluoro-phenyl)-1,2-dihydro-4-hydroxy-5-dimethylamino-1-methyl-2-oxo-quinoline-3-carboxamide, 1H NMR (CDCl$_3$) δ (major form) 2.66 (3H, s), 2.78 (3H, s), 3.44 (3H, s), 3.53 (3H, s), 6.80 (1H, m), 6.96 (1H, m), 7.09–7.28 (3H, m), 7.40 (1H, t), 16.4 (1H, s, broad). 13C NMR (CDCl$_3$) δ 29.9 (CH3), 36.1 (CH3), 45.6 (CH3), 46.7 (CH3), 109.1 (C), 109.7 (C), 113.6 (CH), 114.6 (CH), 115.6 (CH), 116.5 (CH), 116.9 (CH), 131.7 (CH), 132.6 (C), 141.3 (C), 151.1 (C), 155.0 (C), 157.9 (C), 160.8 (C=O), 161.7 (C), 166.2 (C=O). ESI MS/MS [M+H]$^+$ 388, fragment 245.

N-methyl-N-(4-methyl-phenyl)-1,2-dihydro-4-hydroxy-5-nitro-1-methyl-2-oxo-quinoline-3-carboxamide.

EXAMPLE 5

N-Methyl-N-(4-trifluoromethyl-phenyl)-1,2-dihydro-4-hydroxy-5-methoxy-1-methyl-2-oxo-quinoline-3-carboxamide (Method B)

To an ice-cold solution of 1,2-dihydro-4-hydroxy-5-methoxy-1-methyl-2-oxo-quinoline-3-carboxylic acid (8 g, 0.032 mol), triethylamine (15.5 ml, 0.11 mol) and 4-trifluoromethyl-N-methylaniline (6.1 g, 0.035 mol) in 150 ml of dichloromethane, a solution of thionyl chloride (3.0 ml, 0.042 mol) in 10 ml of dichloromethane was added dropwise during 0.5 hours. The stirring was continued at 4° C. for 4 hours. The solution was diluted with 10 ml of dichloromethane, washed with cold 1 M sulfuric acid and then extracted with 1 M sodium hydroxide. The pH of the aqueous phase was adjusted to 8–8.5, and the aqueous solution was clarified by filtration and then acidified with hydrochloric acid to pH 4. On standing a crystalline precipitate was formed which was filtered off, washed with water and dried to give the title compound (8.5 g), yield 65%.

1H NMR (CDCl$_3$) δ 3.48 (3H, s), 3.54 (3H, s), 4,06 (3H, s), 6.70 (1H, d), 6.94 (1H, d), 7.46 (1H, t), 7.50 (4H, broad signal). 13C NMR (CDCl$_3$) δ 29.8 (CH3), 36.9 (CH3), 56.9 (CH3), 103.5 (CH), 104.2 (C), 108.7 (CH), 109.5 (C), 117.3+121.7+126.0+130.3 (C), 125.8+125.9+125.9+126.0 (CH), 126.3 (CH), 127.9+128.4+128.9+129.4 (C), 131.8 (CH), 141.4 (C), 146.7 (C), 157.2 (C), 158.0 (C), 160.3 (C), 165,0 (C); some peaks are multiplets due to F-coupling. ESI MS/MS [M+H]$^+$ 407, fragment 232.

In essentially the same manner the following compounds were obtained from the corresponding starting materials:

N-methyl-N-(4-azido-phenyl)-1,2-dihydro-4-hydroxy-5-chloro-1-methyl-2-oxo-quinoline-3-carboxamide, 1H NMR (CDCl$_3$) δ 3.39 (3H, s), 3.45 (3H, s), 6.89 (1H, d), 7.12–7.27 (5H, m), 7.43 (1H). 13C NMR (CDCl$_3$) δ 30.6 (CH3), 39.1 (CH3), 105.5 (C), 113.4 (C), 114.0 (CH), 119.9+119.9 (CH), 126.2 (CH)5 127.8+127.8 (CH), 132.5 (CH), 139.1 (C), 141.4 (C), 143.3 (C), 158.6 (C=O), 166.7 (C), 169.9 (C=O).

N-ethyl-N-(4-azido-phenyl)-1,2-dihydro-4-hydroxy-5-chloro-1-methyl-2-oxo-quinoline-3-carboxamide, N-methyl-N-(4-azido-phenyl)-1,2-dihydro-4-hydroxy-5,6-methylenedioxy-1-methyl-2-oxo-quinoline-3-carboxamide, N-ethyl-N-(4-azido-phenyl)-1,2-dihydro-4-hydroxy-5,6-methylenedioxy-1-methyl-2-oxo-quinoline-3-carboxamide, N-methyl-N-(4-chloro-phenyl)-1,2-dihydro-4-hydroxy-5-nitro-1-methyl-2-oxo-quinoline-3-carboxamide, N-Methyl-N-(4-methoxy-phenyl)-1,2-dihydro-4-hydroxy-5-nitro-1-methyl-2-oxo-quinoline-3-carboxamide, 1H NMR (CDCl$_3$+TFA) δ 3.45 (3H, s), 3.62 (3H, s), 3.78 (3H, s), 6.81 (2H, d), 7.18 (2H, d), 7.33 (1H, d), 7.54 (1H, d), 7.72 (1H, t). 13C NMR (CDCl$_3$+TFA) δ 31.1 (CH3), 39.0 (CH3)) 55.6 (CH3), 107.3 (C), 108 (C broad), 114.7+114.7 (CH), 117.6 (CH), 117.9 (CH), 126.9+126.9 (CH), 132.7 (CH), 134.9 (C), 140.4 (C), 148.1 (C), 159.1 (C), 159.9 (C), 167.5 (CO). ESI MS/MS [M+H]$^+$ 384, fragment 138+247.

Pharmacological Methods

Acute Experimental Autoimmune Encephalomyelitis (aEAE).

SJL/N female mice, 8 weeks of age, were used for the experiments. Mouse spinal cord homogenate (MSCH) was obtained from 8 to 12 weeks-old C57B1/6 female mice. The tissue was homogenized on ice and diluted in cold PBS. Incomplete Freund's containing 1 mg/mil M. tuberculosis hominis H37Ra was emulsified with an equal volume of MSCH to give a final concentration of 10 mg/ml of MSCH. The inoculum volume of 0.1 ml was injected intradermally at the base of the tail. Pertussis toxin was injected i.p. at day 0 and 3 after immunization. Treatment was given per os daily either at day 3 to 12 post-immunization or days 3 to 7 and 10 to 12. Control animals received saline. The animals, eight per dose group, were scored for clinical signs of paralytic disease on a scale from 0 to 5 in the following way: 0, normal; 1, limp tail; 2, hind limb paresis; 3 hind limb paralysis and limp foreleg; 4, bilateral hind and fore limb paralysis; 5, death. Clinical scores were monitored at day 7 and daily from day 9 until the end of the experiment at day 14. Treatment effects were calculated as percent inhibition of clinical scores compared to saline treated controls.

Collagen Induced Arthritis.

DBA/1 male mice between 8 to 10 weeks of age were used for the experiments. On day 0 the mice were immunized intradermally at the base of the tail with bovine type II collagen (100 μg/mouse) in Freund's complete adjuvant. The treatment was given per os daily on days 3 to 7, 10 to 14, 17 to 21, 24 to 28 and 31 to 35. Fifteen days after immunization mice were inspected for signs of arthritis. The animals were inspected three times a week. Every second or third day individual paws of the arthritic animals were scored by a scale from 0–4 (0=no arthritis, 1=arthritis in one of the interphalangeal, metatarsoplhalangeal or intercarpal joints, 2 =two arthritic joints, 3=three arthritic joints, 4=as in 3 but with more severe redness and swelling of the paw). The score for each paw was added to give a maximal attainable score of 16 for each mouse.

Ovalbumin-induced Lung Inflammation.

C57B1/6 female mice between 10 to 14 weeks of age were used for the experiments, 10 mice/group. The mice were sensitized with ovalbumin (OA) in aluminium hydroxide in a volume of 0.2 ml inoculated i.p. Treatment was given at day 0 to day 16. Control mice received saline. Fourteen days after the OA sensitization mice were exposed for 20 minutes to an aerosol of 1.5% w/v of OA in saline produced by a nebulizer. Vehicle-challenged control mice were exposed to saline. Seventy-two hours after OA/vehicle challenge, mice were anaesthetized and bronchoalveolar lavage was performed by instilling 0.5 ml ice-cold phosphate buffered saline (PBS) into the lungs twice. Total cell counts were determined and differential counts were made based on identification of eosinophils, monocytes/alveolar macrophages, lymphocytes and neutrophils. Eosinophil infiltration into the lung tissue was evaluated by histochemical methods on frozen lung sections using diaminobenzidine tetrahydrochloride (DAB).

Teratogenic Effects in the Rat.

The compounds were administered subcutaneously to female rats during pregnancy, i.e., day 8 to 14 of pregnancy. The rats were caesarean sectioned and necropsied on day 20 after fertilization. The fetuses were examined for external and internal abnormalities.

Beagle Pain Syndronie (BPS).

The compounds were administered intravenously to beagle dogs. The dosage was given for five consecutive days. The dogs were evaluated for clinical and laboratory signs of the pain syndrome, e.g., fever, increased erythrocyte sedimentation rate (ESR), alkaline phosphate (AP), induction of acute phase proteins and vasculitis.

Among preferred compounds are N-methyl-N-(4-azidophenyl)-1,2-dihydro-4-hydroxy-5-chloro-1-methyl-2-oxoquinoline-3-carboxamide and N-methyl-N-(4-methoxyphenyl)-1,2-dihydro-4-hydroxy-5-dimethylamino-1-methyl-2-oxo-quinoline-3-carboxamide hereinafter called Compound A and B, respectively. Roquinimex is included as a reference compound hereinafter called Compound C.

aEAE Inhibition

| Dose, mg/kg p.o. | % aEAE inhibtion | | |
|---|---|---|---|
| | Compound A (invention) | Compound B (invention) | Compound C (reference) |
| 0.2 | 90 | | 35 |
| 1 | 97 | 93 | 40 |
| 5 | | | 69 |

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, aerosols for inhalations, sterile solutions for parental administration, suppositories for rectal administration or suitable topical formulations. Conventional procedures for the selection and preparation of suitable pharmaceutical formulations are described, for example, in "Pharmaceuticals—The Science of Dosage Form Design", M. B. Aulton, Churchill Livingstone, 1988.

A suitable daily dose for use in the treatment of MS is contemplated to vary between 0.0005 mg/kg to about 10 mg/kg body weight, in particular between 0.005 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

References

1. Talal, N.: Autoimmune diseases. In: Roitt, I. M. and Delves, P. J. (eds.) Encyclopedia of Immunology, pp. 195–198. Academic Press, 1992.
2. Prineas, J. W.: The neuropathology of multiple sclerosis. In: Koetsier, J. C. (ed.) Handbook of Clinical Neurology, pp. 213–257. Elsevier Science Publ., Amsterdam, 1985.
3. Tarkowski, A., Gunnarsson, K., Nilsson. L.-Å., Lindholm, L. and Stålhandske, T. Successful treatment of autoimmunity in MRL/1 mice with LS2616, a new immunomodulator. Arthritis Rheum. 29(11): 1405–1409, 1986.
4. Larsson, E.-L., Joki, A.-L. and Stalhandske, T. Mechanism of action of the new immunomodulator LS2616 on T-cell responses. Int J Immunopharmacol 9(4): 425–31, 1987.
5. Wanders, A., Larsson, E., Gerdin, B. and Tufveson G. Abolition of the effect of cyclosporine on rat cardiac allograft rejection by the new immunomodulator LS-2616 (Linomide). Transplantation 47(2): 216–217, 1989.
6. Kalland, T. Regulation of natural killer progenitors: studies with a novel immunomodulator with distinct effects at the precursor level. J Immunol 144(11): 4472–4476, 1990.
7. Gonzalo, J. A., González-Garcia, A., Kalland, T., Hedlund, G., Martinez, C. and Kroemer, G. Linomide, a novel immunomodulator that prevents death in four models of septic shock. Eur J Immunol 23: 2372–2374, 1993.
8. Karussis, D. M., Lehmann, D., Slavin, S. et al. Treatment of chronic-relapsing experimental autoimmune encephalomyelitis with the syntethic immunomodulator Linomide (quinoline-3-carboxamide). Proc Natl Acad Sci USA 90: 6400–6404, 1993.
9. Gonzalo, J. A., González-Garcia, A., Kalland, T. et al. Linomide inhibits programmed cell death of peripheral T cells in vivo. Eur J Immunol. 24: 48–52, 1994.
10. Gross, D. J., Sidi, H., Weiss, L., Kalland, T., Rosenmann, E. and Slavin, S. Prevention of diabetes mellitus in non-obese diabetic mice by Linomide, a novel immuno-modulating drug. Diabetologia 37: 1195–1201, 1994.
11. Karussis, D. M., Lehmannn, D., Brenner, T. et al. Immunomodulation of experimental autoimmune myasthenia gravis with Linomide. J Neuroimmunol 55(2): 187–193, 1994.
12. Bai, X. F., Shi, F. D., Zhu, J., Xiao, B. G., Hedlund, G. and Link, H. Linomide-induced suppression of experimental autoimmune neuritis is associated with down-regulated macrophage functions. J Neuroimmunol 76: 177–184 1997.
13. Karussis, D. M. Meiner, Z., Lehmann, D. et al. Treatment of secondary progressive multiple sclerosis with the immunomodulator Linomide. Neurology 47: 341–346, 1996.
14. Andersen, O., Lycke, J., Tollesson, P. O. et al. Linomide reduces the rate of active lesions in relapsing-remitting multiple sclerosis. Neurology 47: 895–900, 1996.
15. Kelly. D. F. Grimsell, C. S. G. and Kenyon, C. J. Polyarteritis in the dog: A case report. Vet Record 92: 363–366, 1973.
16. Harcourt, R. A. Polyarterites in a colony of beagles. Vet Record 102: 519–522, 1978.

What is claimed is:

1. N-methyl-N-(4-methoxy-phenyl)-1,2-dihydro-4-hydroxy-5-dimethylamino-1-methyl-2-oxo-quinoline-3-carboxamide.

2. A pharmaceutical composition comprising as active ingredient a therapeutically effective amount of a compound having the formula (I) of claim 1 together with a pharmaceutical carrier.

3. A pharmaceutical composition according to claim 2 in unit dosage form sufficient to provide a daily dose of the active substance of 0.0005 mg/kg to about 10 mg/kg body weight.

4. A pharmaceutical composition according to claim 2 in unit dosage form sufficient to provide a daily dose of the active substance of 0.005 to 1 mg/kg body weight.

5. A method of treating a mammal suffering from pathologic inflammation or a disease result in from autoimmunity comprising
   administering to said mammal an amount sufficient for said treatment of the compound of claim 1 or a pharmaceutically acceptable salt or tautomer thereof.

6. The method according to claim 5 wherein said mammal is one suffering from multiple sclerosis (MS).

7. The method according to claim 5 wherein said mammal is one suffering from insulin-dependent diabetes mellitus (IDDM).

8. The method according to claim 5 wherein said mammal is one suffering from systemic lupus erythematosus (SLE).

9. The method according to claim 5 wherein said mammal is one suffering from rheumatoid arthritis (RA).

10. The method according to claim 5 wherein said mammal is one suffering from inflammatory bowel disease (IBD).

11. The method according to claim 5 wherein said mammal is one suffering from psoriasis.

12. The method according to claim 5 wherein said mammal is one suffering from inflammatory respiratory disorder.

13. The method according to claim 5 wherein said mammal is one suffering from asthma.

14. The method according to claim 5 wherein said mammal is one suffering from atherosclerosis.

15. The method according to claim 5 wherein said mammal is one suffering from stroke.

16. The method according to claim 5 wherein said mammal is one suffering from Alzheimer's disease.

17. The method according to claim 5, wherein said amount is 0.0005 mg/kg to about 10 mg/kg body weight.

18. The method according to claim 5, wherein said amount is 0.005 mg/kg to about 1 mg/kg body weight.

* * * * *

UNITED STATES PATENT AND TRADEMARK OFFICE
CERTIFICATE OF CORRECTION

PATENT NO. : 6,605,616 B1
DATED : August 12, 2003
INVENTOR(S) : Bjork et al.

It is certified that error appears in the above-identified patent and that said Letters Patent is hereby corrected as shown below:

Column 1,
Line 30, delete "lupuis" and insert therefor -- lupus --;
Line 52, delete "sheaths" and insert therefor -- sheets --;

Column 3,
Line 49, delete "parca" and insert therefor -- para --;

Column 4,
Line 9, delete "encephalonmyelitis" and insert therefor -- encephalomyelitis --;

Column 6,
Line 58, delete "organ" and insert therefor -- organic --;

Column 7,
Line 43, delete "dimethylacetanide" and insert therefor -- dimethylacetamide --;

Column 8,
Line 49, delete "7.40" and insert therefor -- 7.50 --;

Column 10,
Line 21, delete "metatarsoplhalangeal" and insert therefor -- metatarsophalangeal --.

Signed and Sealed this

Twenty-eighth Day of October, 2003

JAMES E. ROGAN
*Director of the United States Patent and Trademark Office*